US008942662B2

(12) United States Patent
Pan et al.

(10) Patent No.: US 8,942,662 B2
(45) Date of Patent: Jan. 27, 2015

(54) SYSTEM AND METHOD TO PREDICT AND AVOID MUSCULOSKELETAL INJURIES

(71) Applicant: The United States of America as represented by the Secretary of the Department of Health and Human Services, Centers for Disease Control and Prevention, Atlanta, GA (US)

(72) Inventors: Christopher S. Pan, Morgantown, WV (US); Shengke Zeng, Lansdale, PA (US); Bryan Wimer, Morgantown, WV (US)

(73) Assignee: The United States of America, as represented by the Secretary, Department of Health and Human Services, Center for Disease Control and Prevention, Washington, DC (US)

(*) Notice: Subject to any disclaimer, the term of this patent is extended or adjusted under 35 U.S.C. 154(b) by 0 days.

(21) Appl. No.: 13/768,290

(22) Filed: Feb. 15, 2013

(65) Prior Publication Data
US 2013/0217352 A1    Aug. 22, 2013

Related U.S. Application Data

(60) Provisional application No. 61/599,525, filed on Feb. 16, 2012.

(51) Int. Cl.
*G08B 21/02* (2006.01)
*A61B 5/00* (2006.01)
(Continued)

(52) U.S. Cl.
CPC ............... *G08B 21/02* (2013.01); *A61B 5/746* (2013.01); *A61B 5/747* (2013.01); *A61B 5/0024* (2013.01);
(Continued)

(58) Field of Classification Search
CPC ............ H04J 1/14; H04M 7/16; G08B 21/22; A61B 5/0002
USPC ..................... 340/539.11, 539.12, 540, 573.1; 455/404.1, 403, 408
See application file for complete search history.

(56) References Cited

U.S. PATENT DOCUMENTS 7,918,887 B2 *  4/2011  Roche ........................ 623/17.11
8,149,126 B2    4/2012  Little et al.
(Continued)

FOREIGN PATENT DOCUMENTS

WO    WO2010/099066    9/2010

*Primary Examiner* — Cong Tran
(74) *Attorney, Agent, or Firm* — Gifford, Krass, Sprinkle, Anderson & Citkowski, P.C.

(57) ABSTRACT

A miniaturized, ruggedized, field-deployable Portable Exposure Assessment System (PEAS) is used to remotely monitor workers and provide real-time warning of exposure to musculoskeletal injury conditions via alarm and smart-phone transmission. The PEAS unit wirelessly acquires exposure data from sensors; conducts initial data analysis; triggers proximal and remote alarms; sends out text messages with abnormal data, GPS locations, and time stamps to a safety office; and saves data for more extensive assessment. Sensor technology is used in this field-deployable system to simultaneously measure and collect the body loads and awkward postures imposed by package handling as well as driving-related, low-frequency vibration exposures. Wireless technology is used to set up wireless communication links between the sensors and a data logger and between the data logger and a smart phone with GPS, date/time stamp and text messaging capabilities.

22 Claims, 9 Drawing Sheets

(51) Int. Cl.
*A61B 5/103* (2006.01)
*A61B 5/11* (2006.01)

(52) U.S. Cl.
CPC ............. *A61B 5/1036* (2013.01); *A61B 5/1112* (2013.01); *A61B 5/1117* (2013.01); *A61B 5/1121* (2013.01); *A61B 5/7275* (2013.01); *A61B 5/6829* (2013.01); *A61B 5/6823* (2013.01); *A61B 5/6824* (2013.01); *A61B 2503/20* (2013.01)
USPC ................ 455/404.1; 340/539.12; 340/573.1

(56) References Cited

U.S. PATENT DOCUMENTS

| | | | |
|---|---|---|---|
| 8,280,517 | B2 | 10/2012 | Skelton et al. |
| 8,284,070 | B2 | 10/2012 | Chaudhari et al. |
| 8,347,094 | B2 * | 1/2013 | Singh ........................... 713/169 |
| 8,547,248 | B2 * | 10/2013 | Zdeblick et al. ......... 340/870.28 |
| 2007/0250286 | A1 | 10/2007 | Duncan et al. |
| 2009/0124870 | A1 * | 5/2009 | Arends et al. ................. 600/301 |
| 2009/0231125 | A1 * | 9/2009 | Baldus et al. ............. 340/539.12 |
| 2011/0269414 | A1 * | 11/2011 | Falck et al. .................... 455/100 |
| 2012/0169491 | A1 * | 7/2012 | Chang et al. ................. 340/531 |
| 2012/0259650 | A1 | 10/2012 | Mallon et al. |

* cited by examiner

Elbow Position (x1, y1, z1) relative to Shoulder Joint:

$x1 = r1 \sin α1 \cos β1$
$y1 = r1 \sin α1 \sin β1$
$z1 = r1 \cos α1$

Wrist Position (x2, y2, z2) relative to Elbow Joint:

$x2 = r2 \sin α2 \cos β2$
$y2 = r2 \sin α2 \sin β2$
$z2 = r2 \cos α2$

Wrist Position (x, y, z) relative to Shoulder Joint:

$x = x1 + x2$
$y = y1 + y2$
$z = z1 + z2$

Wrist horizontal distance from shoulder joint:

$R = (x^2 + y^2)^{1/2}$ $α1$ and $β1$: Elevation and Azimuth Angles in X1, Y1, Z1 Coordinate
$α2$ and $β2$: Elevation and Azimuth Angles in X2, Y2, Z2 Coordinate
$r1$: Upper Arm
$r2$: Lower Arm

The torso vibration accelerations on 3 axes are measured and digitized by the accelerometer AIS326DQ and sent to the MCU MSP430F2274.

The sampling rate of the accelerometer is 100 Hz to measure ~50 Hz vibration.

The MSP430F2274 calculate the RMS accelerations on 3 axes continuously, and transmits the RMS acceleration data to the data logger via a 915 MHz RF Transceiver.

SYSTEM AND METHOD TO PREDICT AND AVOID MUSCULOSKELETAL INJURIES

REFERENCE TO RELATED APPLICATION

This application claims priority from U.S. Provisional Patent Application Ser. No. 61/599,525, filed Feb. 16, 2012, the entire content of which is incorporated herein by reference.

GOVERNMENT INTEREST

The invention described herein may be manufactured, used, and licensed by or for the United States Government.

FIELD OF THE INVENTION

This invention relates generally to systems for measuring worker safety and, in particular, to a portable, field-based, remotely deployed system and method to monitor and provide early warning of exposure to conditions that might lead to musculoskeletal injury.

BACKGROUND OF THE INVENTION

Any worker who lifts and carries objects—such as packages for delivery, construction materials, manufactured goods, or patients—is at risk of musculoskeletal injury. Various methodologies exist that analyze lifting tasks to quantify musculoskeletal risks, such as the National Institute for Occupational Safety and Health (NIOSH) method. One system for applying the NIOSH equation is described in U.S. Pat. No. 5,621,667. This patent describes an instrumented analysis system based on a retractable cable and potentiometer system which can determine the NIOSH equation multipliers indicative of physical parameters related to a lifting task under analysis. However, the system is difficult to implement in a normal working environment since it requires a dedicated space to set up the instrumentation and experienced personnel to operate the system. As such, the system of the '667 Patent is more suited to a laboratory environment than a regular work environment.

Published U.S. Patent Application No. 2007/0250286 describes a motion analysis system that can be used to alert a worker that their current motion is not optimal, upon detection of a specified criterion being exceeded during a performed task. Such a criterion can be calculated by applying common work place safety assessment tools, such as the NIOSH equation, or other similar measures previously mentioned using the collected data. Sensor elements attached to movable body segments record movement parameters including angular velocity and acceleration. A control device receives the movement parameters and determines an overall motion of the movable body segments. The overall motion is analyzed against an acceptable motion model to determine whether the overall motion is within acceptable limits. The sensor elements and control device are lightweight and can be worn during normal movement activities, thereby allowing monitoring of work-based activities, such as lifting or typing.

While it is claimed that the system described in the '286 Application can be used in a number of applications previously relegated to laboratory spaces and dedicated laboratory equipment, the system and method have various shortcomings. As one example, the alarm system is limited and could benefit from other modalities, including wireless transmissions. Further, a more appropriate application of gyroscopes and accelerometers could be deployed to measure body vibrations, spine angle, body posture sway and instability.

U.S. Pat. No. 8,149,126 relates to a system for monitoring the behavior of a subject to detect an incidence of unsafe lifting strategy use or high-risk movement. The system includes a wearable trunk sensor, a wearable thigh sensor, and a portable computing device. The computing device may receive the data from the trunk sensor and/or the thigh sensor via a wireless transceiver. Based on the received data, the computing device determines trunk angle and a thigh angles using a combination of accelerometer and gyroscope data received from the trunk and thigh sensors. Trunk rotation is determined by comparing rotation data obtained from the trunk sensor with data obtained from the thigh sensor. The trunk angle, thigh angle, and/or trunk rotation values are used to calculate a risk level associated with the subject's movement. The system may include additional sensors, such as a weight sensor, to determine the weight of an object being lifted, for example for inclusion in the risk level assessment algorithm. The weight sensors may be shoe borne pressure sensors or pressure sensors mounted into surfaces upon which the subject stands, e.g., a floor, ramp, platform, or truck bed. While the system described in the '126 patent may be useful in some circumstances, the assessments do not take into account hand or arm movements, vibration, or other more sophisticated modalities or computations.

SUMMARY OF THE INVENTION

This invention resides in a portable, field-based, remotely deployed tool to monitor and provide early warning of the exposure of workers to conditions that have a high likelihood of musculoskeletal injury, specifically through the lifting or carrying of items that are too heavy or bulky given the environmental conditions or the body of the worker. Such conditions are known to be associated with high incidence of subsequent slip, trip, and fall injuries, both as a result of injury to the soft tissues of the body and as a result of direct exposure to excess loads. Further injury conditions monitored by the system include those generated by continued exposure to low-level vibrations, as experienced by truck drivers and machinery operators.

The systems, called the Portable Exposure Assessment System (PEAS) is used to remotely monitor workers to instantaneously determine and provide warning of exposure to these injury conditions. The apparatus provides real time notification via alarm and smart-phone transmission, of injury-risk conditions that are likely to lead to musculoskeletal injury, as well as exposure to slip-, trip-, and fall-related traumatic injury. The device is miniaturized, ruggedized, and field deployable, such that it can be worn at worksites without interfering with workers' regular tasks. The portable unit, including a data logger, is approximately the size of a cellular telephone and will use comparable technology. Both the worker and any monitoring station can be notified by the alarm.

The PEAS unit acquires exposure data from sensors; conducts initial data analysis; triggers proximal and remote alarms; sends out text messages with abnormal data to a safety officer, GPS locations, and time stamps; and saves data for more extensive assessment. Sensor technology is used in this field-deployable system to simultaneously measure and collect the body loads and awkward postures imposed by package handling as well as driving-related, low-frequency vibration exposures. Wireless technology will be used to set up wireless communication links between the sensors and a data logger and between the data logger and a smart phone with GPS and text messaging capabilities.

The smart phone may be programmed to (1) wirelessly receive commands from the data logger to dial a number and send a text message containing the exposure data that exceed the safety thresholds, the GPS location, the date/time stamps, and the corresponding safety message; and (2) wirelessly receive and store data transmitted from the data logger and transfer these data and the corresponding GPS locations and time stamps to a computer, via a proper computer interface, for further data analysis.

DETAILED DESCRIPTION OF THE INVENTION

Figure 1:
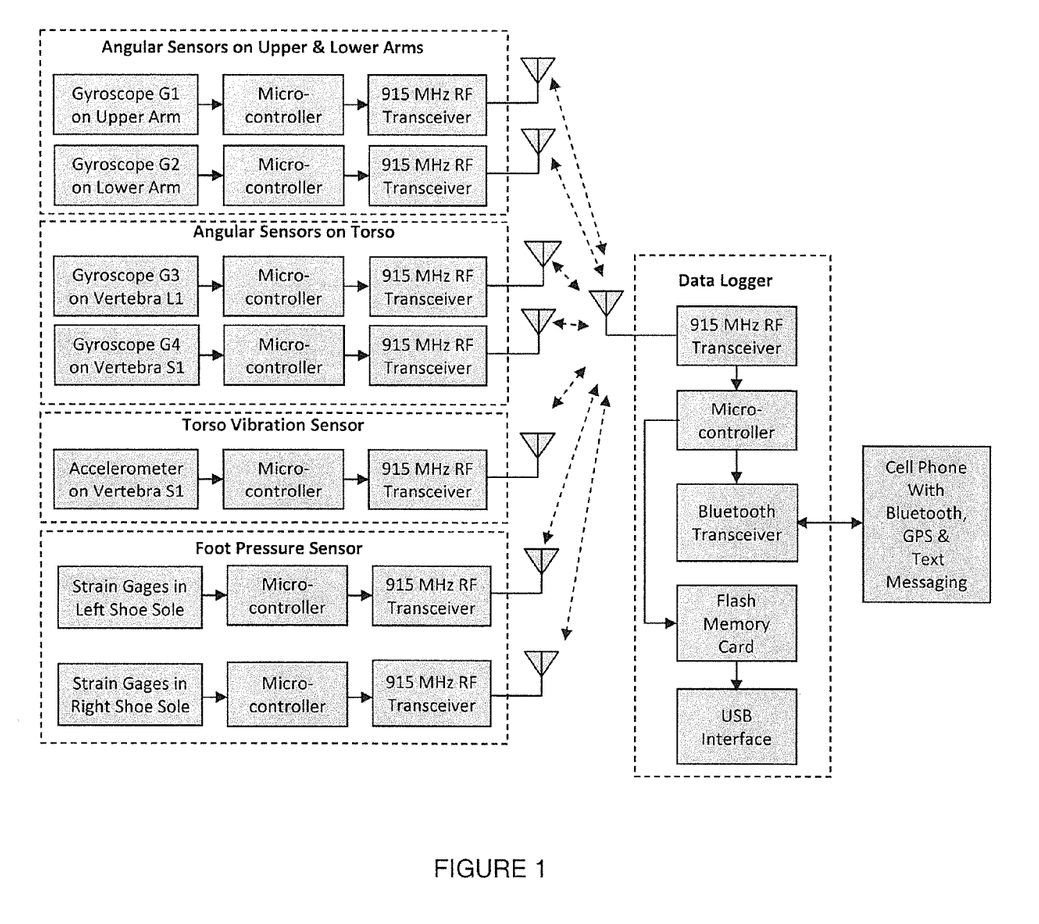
FIG. 1 is a system block diagram of a preferred embodiment of the invention.

As shown in FIG. 1, the PEAS comprises (1) gyroscope position sensors on the upper and lower arms to measure the worker's hand (wrist) positions; (2) gyroscope angular sensor on the worker's torso to measure torso angle; (3) an accelerometer-based torso vibration sensor to measure the vibration experienced by the worker while operating a truck; (4) foot force sensors to measure the load distribution experienced by the worker while carrying packages; (5) a data logger to collect all measured data, conduct necessary real time data processing by comparing the data to predefined safety thresholds stored in memory, save and transfer the data and results of the analysis, and communicate with a smart phone; and (6) a smart phone to (a) wirelessly receive commands from the data logger and send out text messages with abnormal exposure data to a safety officer, GPS location, and date/time information and (b) wirelessly receive the data transmitted from the data logger, store these data with correspondent GPS locations and date/time stamps, and transfer these data. GPS locations and date/time stamps to a computer via a proper computer interface, such as a USB interface.

Figure 2:
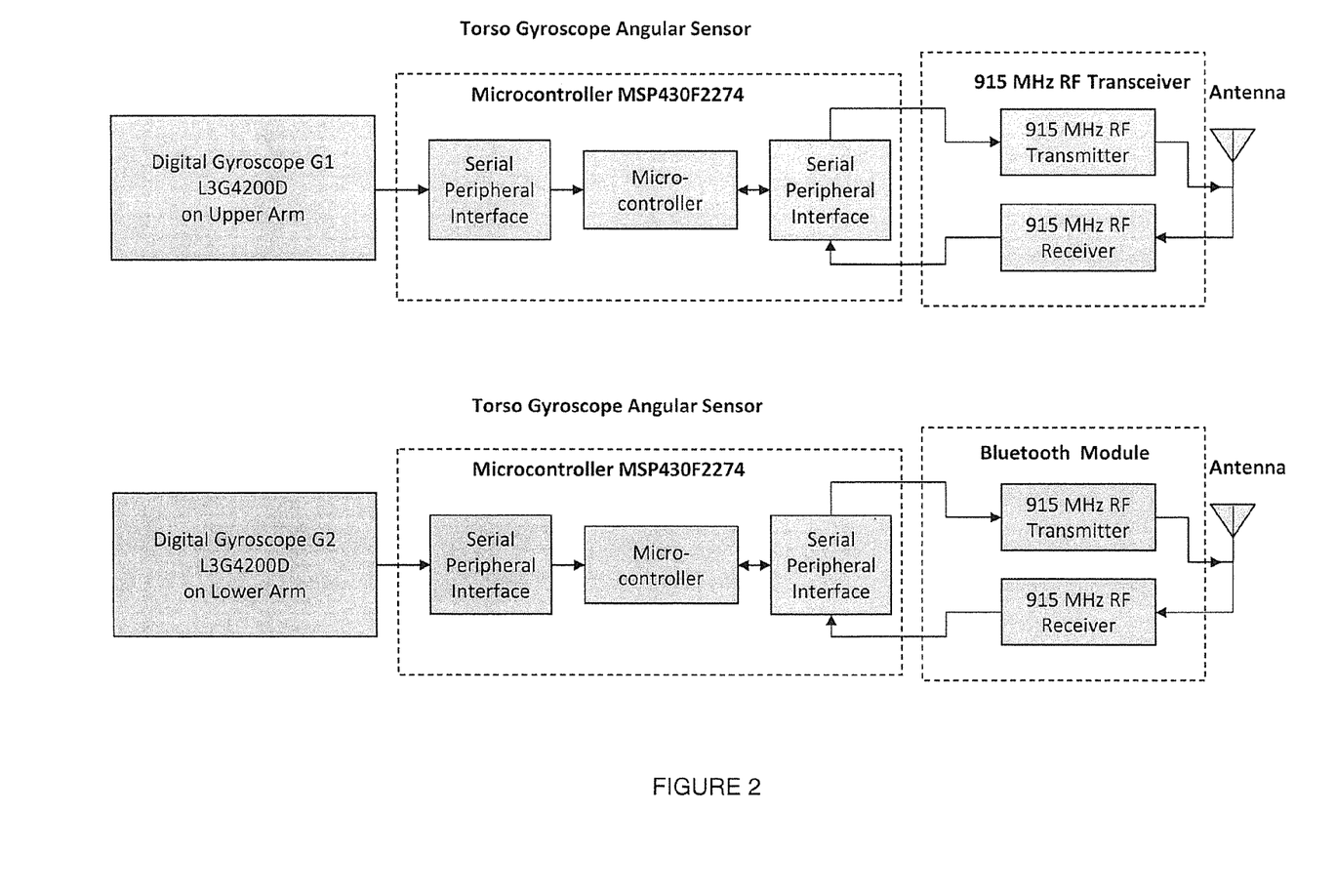
FIG. 2 is a first block diagram of a gyroscope hand position sensor.

Referring now to FIG. 2, the hand (wrist) position sensor is composed of two triaxial gyroscopes (G1 and G2) to measure the angular velocities of the upper arm and lower arm, two microcontrollers to calculate the elbow position relative to the shoulder joint and the wrist position relative the elbow joint, and two radio frequency (RF) transceivers to transmit the elbow and wrist position data to the data logger and receive commands from the logger. The data logger receives these position data and calculates the wrist position relative to the shoulder joint. Two sets of hand position sensors are mounted on the worker's left and right arms to measure the positions of the left and right wrists.

Figure 3:
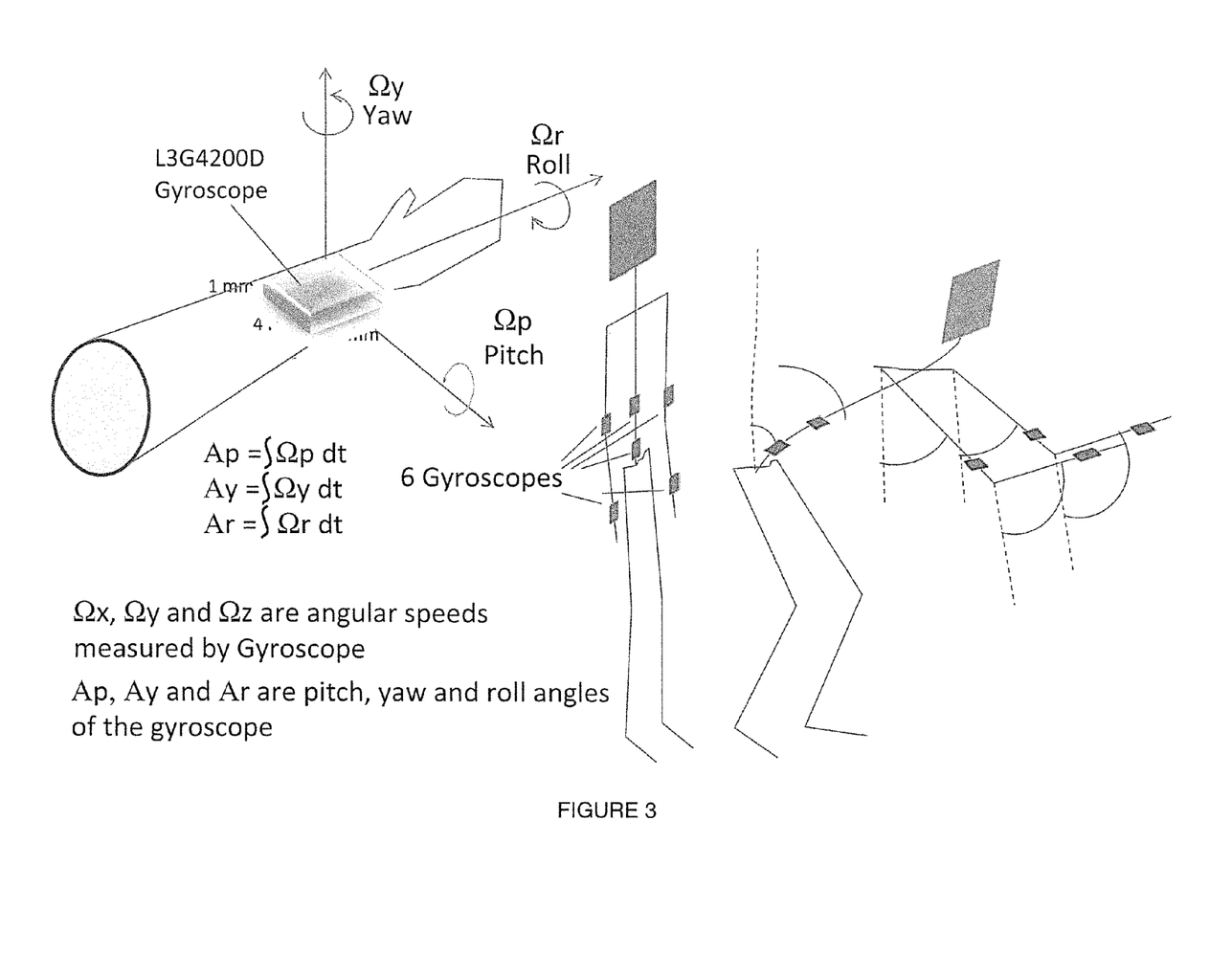
FIG. 3 is a second block diagram of a gyroscope hand position sensor.
Figure 4:
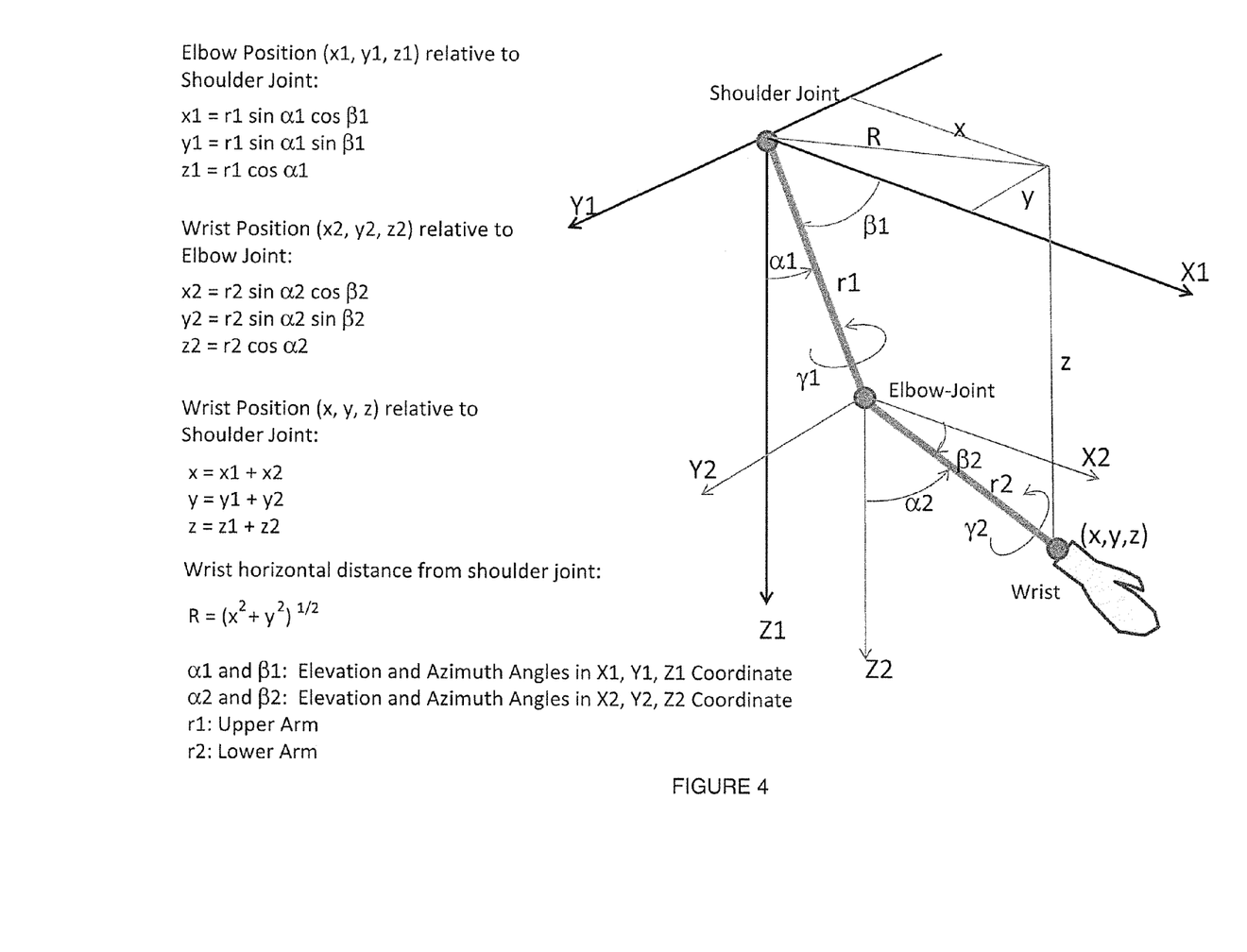
FIG. 4 is a third block diagram of a gyroscope hand position sensor.

To measure the wrist positions relative to the shoulder joint, G1 is mounted near the elbow of the upper arm and G2 is mounted near the wrist of the lower arm. First, G1 measures the elbow's pitch, yaw and roll angular velocities. The microcontroller connected with G1's output in the sensor calculates the elbow's pitch, yaw and roll angles by computing the integral of G1's pitch, yaw and roll angular velocities (FIG. 3). The microcontroller consecutively converts the pitch, yaw and roll angles into the spherical elevation and azimuth angles, and calculates the elbow position relative to the shoulder joint using Equations 1, 2, and 3:

$$x1 = r1 \sin \alpha 1 \cos \beta 1 \quad (1)$$

$$y1 = r1 \sin \alpha 1 \sin \beta 1 \quad (2)$$

$$z1 = r1 \cos \alpha 1 \quad (3)$$

where x1, y1, and z1 are the position coordinates of the elbow relative to the shoulder joint; r1 is the length of the upper arm; α1 and β1 are elevation and azimuth angles of G1 (FIG. 4).

Similar to the calculations in G1, the microcontroller connected with G2's output calculates the wrist position relative to the elbow joint using Equations 4, 5, and 6:

$$x2 = r2 \sin \alpha 2 \cos \beta 2 \quad (4)$$

$$y2 = r2 \sin \alpha 2 \sin \beta 2 \quad (5)$$

$$z2 = r2 \cos \alpha 2 \quad (6)$$

where x2, y2, and z2 are the position coordinates of the wrist relative to the elbow joint; r2 is the length of the lower arm; α2 and β2 are elevation and azimuth angles of G2 (FIG. 4).

The data logger's RF transceiver receives the x1, y1 and z1 position coordinates from G1's RF transceiver and receives the x2, y2 and z2 position coordinates from G2's RF transceiver and the data logger's microcontroller calculates the wrist position relative to the shoulder joint using Equations 7, 8, and 9:

$$x = x1 + x2 \quad (7)$$

$$y = y1 + y2 \quad (8)$$

$$z = z1 + z2 \quad (9)$$

where x, y, and z are the position coordinates of the wrist relative to the shoulder joint (FIG. 4).

Figure 5:
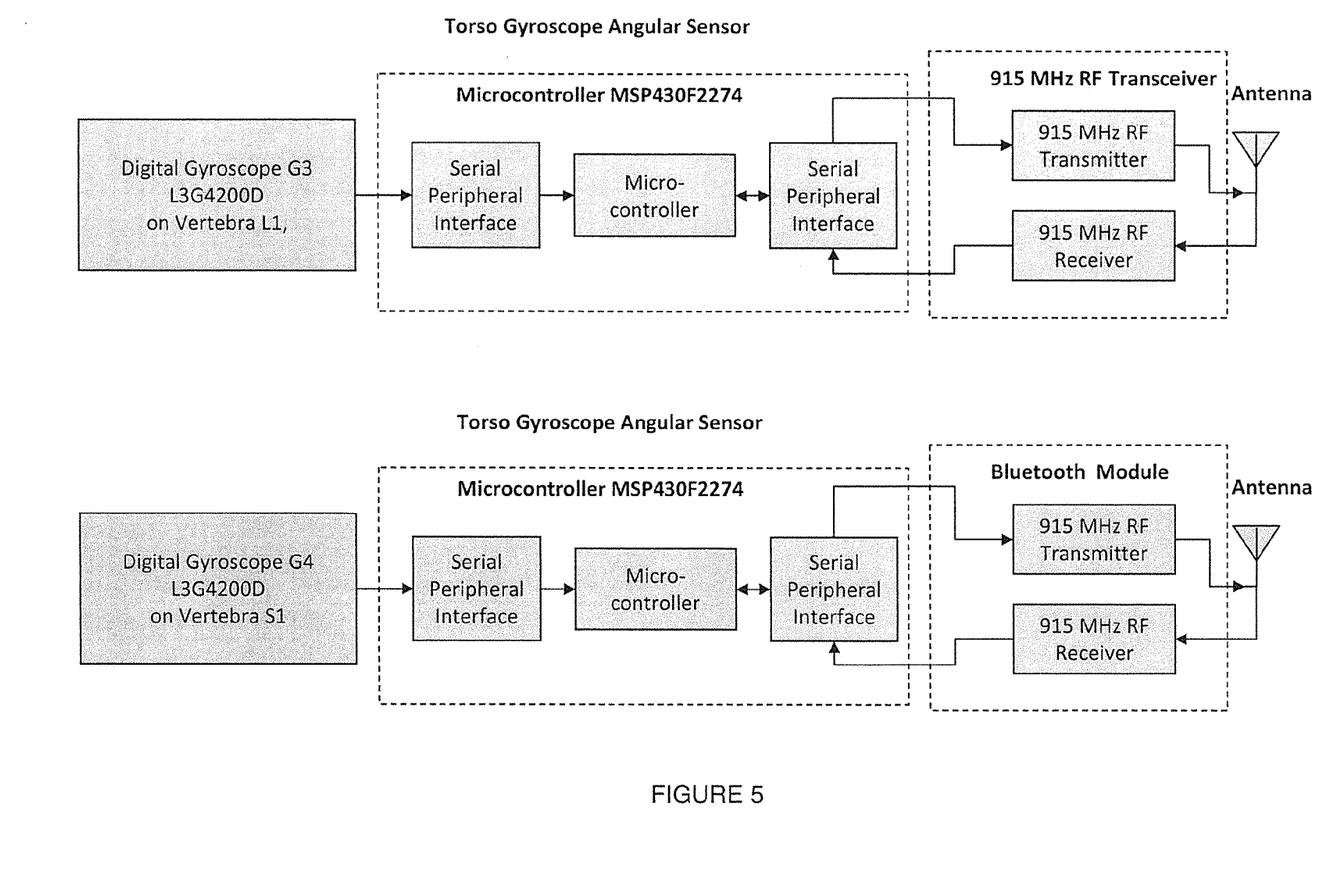
FIG. 5 is a first block diagram of a gyroscope torso angular sensor.

The gyroscope torso angular sensor (FIG. 5) is composed of two triaxial gyroscopes (G3 and G4) to measure the angular velocities of the vertebras L1 and S1, two microcontrollers to calculate the angles of L1 and S1, and two RF transceivers to transmit L1 and S1 angle data to the data logger and receive commands from the logger.

Figure 6:
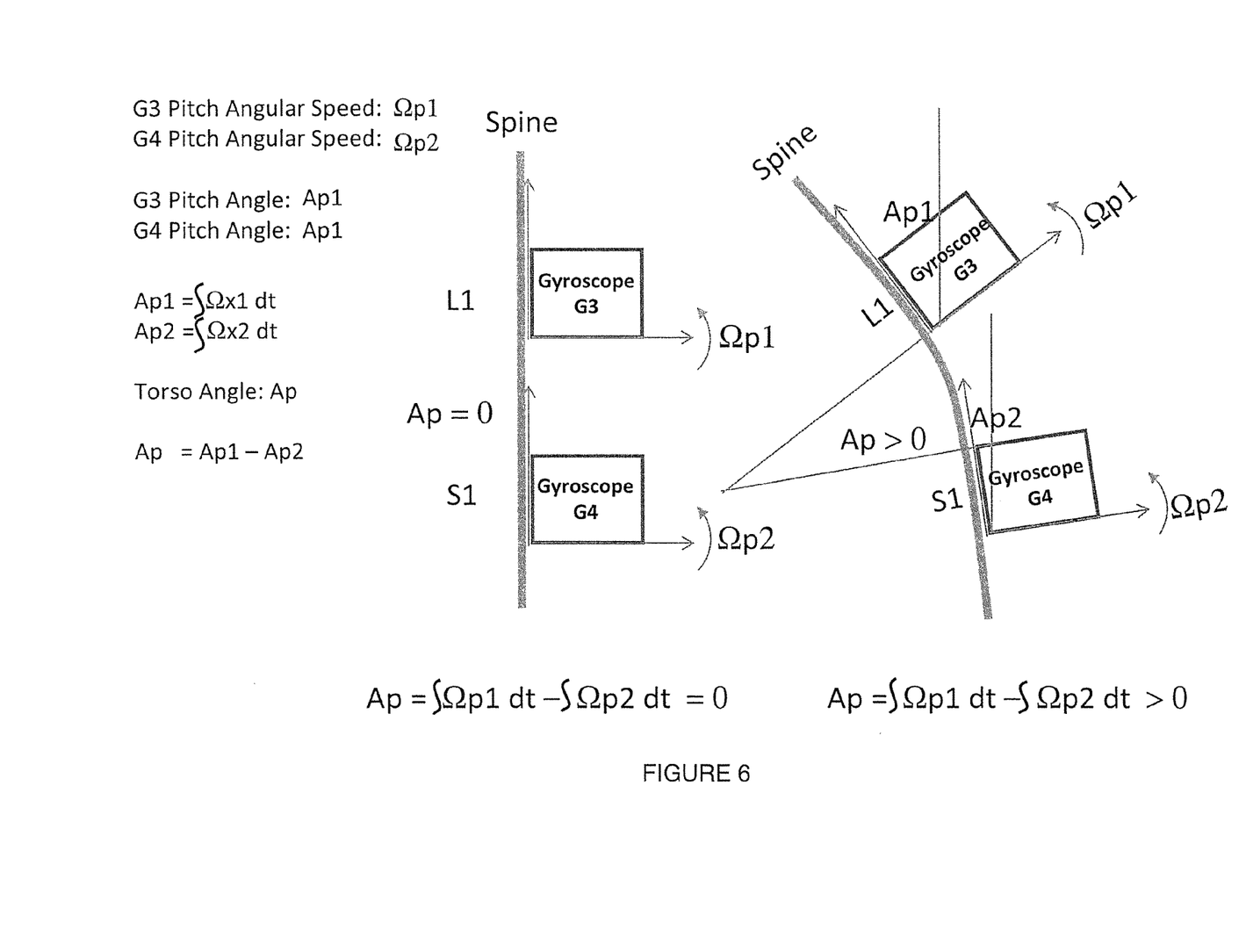
FIG. 6 is a second block diagram of a gyroscope torso angular sensor.

To measure the pitch, yaw and roll angular velocities of the torso, G3 is mounted on vertebra L1 and G4 is mounted on vertebra S1. After G3 measures the pitch, yaw and roll angular velocities of vertebra L1, the microcontroller connected with G3's output in the sensor calculates the pitch, yaw and roll angles of L1 by computing the integral of the pitch, yaw and roll angular velocities. The pitch, yaw and roll angles of vertebra S1 are measured and calculated in the same method. The data logger transceiver receives the L1 and S1 pitch, yaw and roll angles from L1 and S1 transceivers, and calculates the torso pitch, yaw and roll angles. The torso pitch angle is the difference of the L1 and S1 pitch angles, the torso yaw angle is the difference of the L1 and S1 yaw angles, and the torso roll angle is the difference of the L1 and S1 roll angles (FIG. 6).

Figure 7:
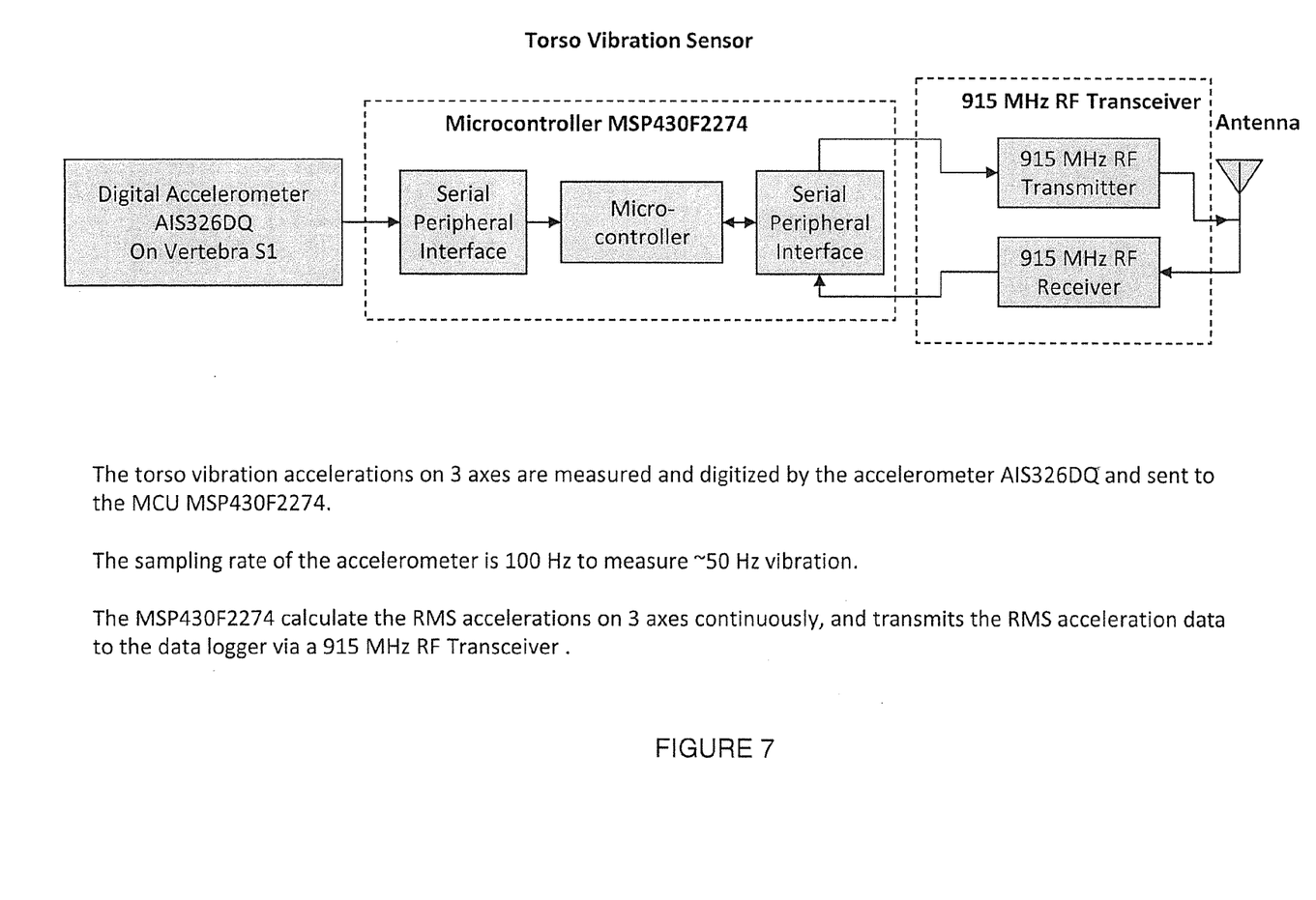
FIG. 7 is a block diagram of an accelerometer torso vibration sensor.

The torso vibration sensor (FIG. 7) captures the acceleration data on the lower back of the worker while operating a truck. The vibration sensor is composed of an accelerometer (sensitivity range <2 g), a microcontroller, and an RF transceiver. The sensor is positioned at the worker's vertebra S1. The accelerometer measures the low-frequency acceleration of the lower back in real time. The microcontroller calculates the root-mean-square (RMS) values of the acceleration in a short RMS period (such as 1 second) and transmits the RMS acceleration data to the data logger at the end of every RMS period.

Figure 8:
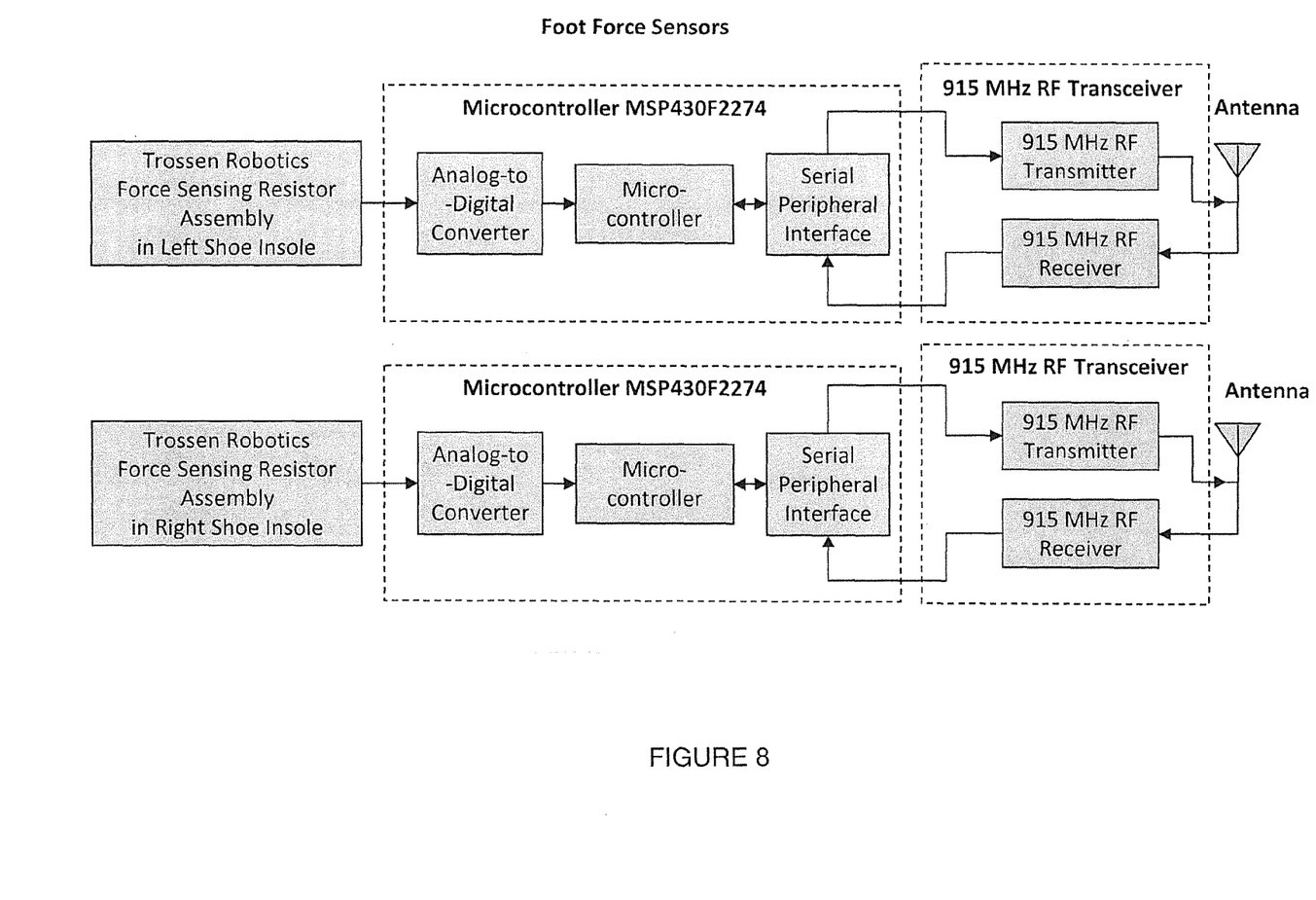
FIG. 8 is a first block diagram of a foot force sensor.
Figure 9:
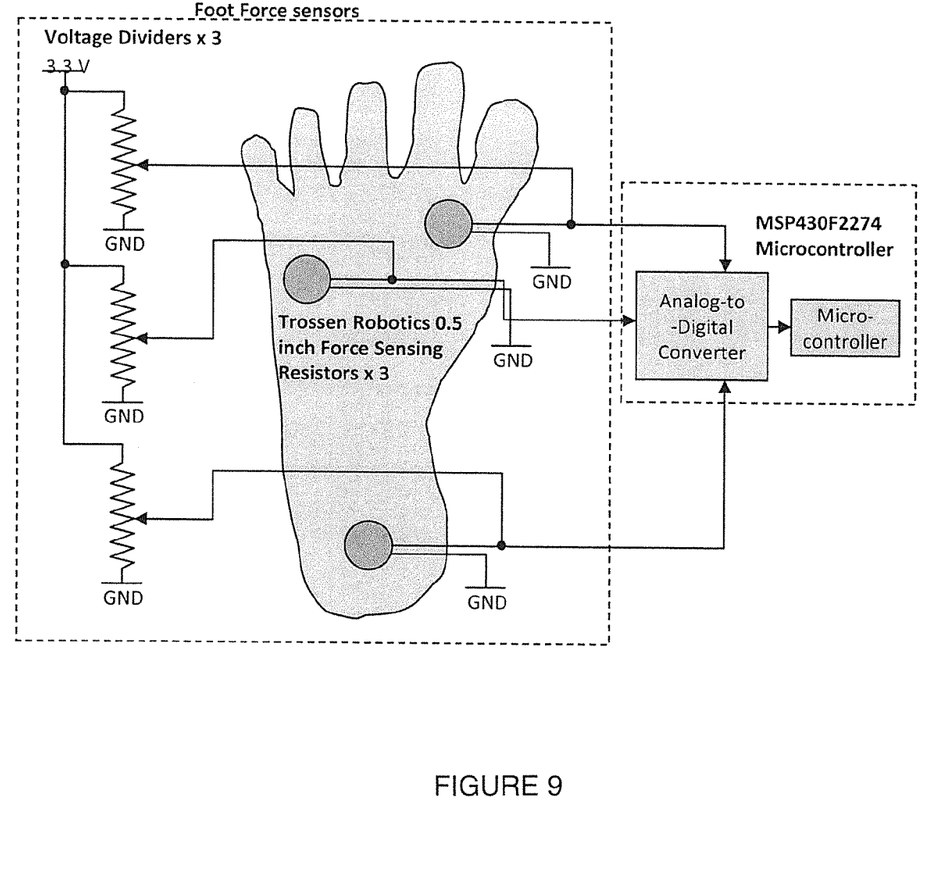
FIG. 9 is a second block diagram of a foot force sensor.

The foot force sensors (FIG. 8) capture foot force experienced by the worker while carrying packages. The foot force sensors consist of two identical subsensor groups for the force sensing on the left and right feet. Each subsensor group is composed of three strain gauge force transducers, a microcontroller, and an RF transceiver. The force sensors are mounted on the insoles of the worker's shoes as shown in FIG. 9. The force sensors measure the worker's foot force distribution on the shoe soles in real time. The microcontroller samples the foot force distribution data and transmits the data to the data logger via the RF transceiver.

The data logger acts as the controller of the PEAS system. It can be placed anywhere around the worker. It is composed of a microcontroller, a flash memory integrated circuit (IC), an RF transceiver, and a Bluetooth wireless module, which is wirelessly linked to a smart phone. The data logger wirelessly communicates with the hand position sensors, the torso angular sensor, the torso vibration sensor, and the foot force sensors via its RF transceiver. The data logger receives the data transmitted from the sensors, saves the data on its flash memory IC, processes the data, and compares the processed data with the predefined safety thresholds to determine excessive exposures in real time. The data logger wirelessly communicates with the smart phone via its Bluetooth wireless module.

The processed data are stored on the data logger's flash memory IC. These data can be transmitted to the smart phone via the Bluetooth module, and transferred to a computer via computer interface. The smart phone stores the processed data with the corresponding GPS locations and time stamps. After the field data collection is complete, the smart phone transfers the whole set of stored data to a computer via a computer interface, such as a USB interface, for further data analysis. The data logger can wirelessly control the smart phone to dial a number and send an emergency message to safety officer via an alarm mechanism.

The alarm mechanism may include an audible/visual alarm group inside the data logger, and the text messaging, GPS and time stamp functions of the smart phone. If one or more real time exposure data exceed the predefined safety threshold(s), the data logger sets off its audible and/or visual alarms. In the meantime, the data logger activates the smart phone via its Bluetooth module to dial an emergency number and send out a text message containing a prerecorded safety message to a safety officer, along with abnormal data, corresponding GPS locations, and time stamps.

The anticipated use of the PEAS system will be in the monitoring of industrial tasks that currently are associated with high rates of personal injury and workers' compensation payments from worker exposure to occupational conditions associated with repeated or continual lifting of heavy packages, tools, building materials, and manufacturing items. Targeted industrial sectors include construction, package delivery, manufacturing, healthcare, and trucking. Sources of injury include falls to the same level, lifting-induced musculoskeletal disorders, and vibration-induced injury. It is anticipated that end users will be safety officers within the environmental, safety, and health departments of large corporations with high workers' compensation premiums and employees with responsibility for safety and health within smaller corporations.

The invention claimed is:

1. A system for assessing whether a user is exposed to conditions which might lead to a musculoskeletal injury, comprising:
   a plurality of body-worn sensors, each sensor being operative to measure conditions associated with body loading, posture or vibration and transmit a wireless signal containing data about such conditions;
   a portable, body-worn data logger including a wireless receiver for receiving the signals transmitted by the sensors, the data logger including a processor and a memory for storing predefined safety thresholds, the processor being operative to calculate hand (wrist) positions and torso angles, and compare the data received from the sensors or retrieved from its calculation results to the safety thresholds to determine if the user's body loading, posture or vibration may lead to a musculoskeletal injury; and
   an alarm generated in response to a determination that a risk of musculoskeletal injury is present.

2. The system of claim 1, including a body-worn alarm and a remote alarm in wireless communication with the data logger.

3. The system of claim 1, wherein the data logger is operative to generate a remote alarm to a smart phone with GPS, data/time stamps and text messaging capabilities.

4. The system of claim 1, wherein the sensors include one or more of the following:
   angular sensors disposed on the upper and lower arms,
   angular sensors disposed on the torso,
   a vibration sensor disposed on the torso, and
   foot force sensors.

5. The system of claim 4, including right and left wireless gyroscope angular measurement sensors to determine the hand (wrist) positions of a user.

6. The system of claim 5, wherein each wireless gyroscope angular measurement sensor includes a triaxial gyroscope (G1, G2) to measure the angular velocities of the upper arm and lower arm and a microcontroller to calculate the elbow position relative to the shoulder joint and the wrist position relative the elbow joint.

7. The system of claim 6, wherein:
   each wireless gyroscope angular measurement sensor further includes a radio frequency (RF) transceiver to transmit the elbow and wrist position data to the data logger; and
   the data logger calculates the wrist position relative to the shoulder joint.

8. The system of claim 7, wherein:
   G1 is mounted near the elbow of the upper arm;
   G2 is mounted near the wrist of the lower arm;
   G1 measures the elbow's pitch, yaw and roll angular velocities;
   the microcontroller associated with G1 performs the following operations:
      calculates the elbow's pitch, yaw and roll angles by computing the integral of G1's pitch, yaw and roll angular velocities,
      consecutively converts the pitch, yaw and roll angles into the spherical elevation and azimuth angles, and calculates the elbow position relative to the shoulder joint using the following equations:

$$x1 = r1 \sin \alpha 1 \cos \beta 1 \quad (1)$$

$$y1 = r1 \sin \alpha 1 \sin \beta 1 \quad (2)$$

$$z1 = r1 \cos \alpha 1 \quad (3)$$

where x1, y1, and z1 are the position coordinates of the elbow relative to the shoulder joint, r1 is the length of the upper arm, and α1 and β1 are elevation and azimuth angles of G1.

9. The system of claim 8, wherein:
in the same way to calculate the position coordinates of the elbow relative to the shoulder joint, the microcontroller associated with G2 is operative to calculate the wrist position relative to the elbow joint using the following equations:

$$x2 = r2 \sin \alpha 2 \cos \beta 2 \quad (4)$$

$$y2 = r2 \sin \alpha 2 \sin \beta 2 \quad (5)$$

$$z2 = r2 \cos \alpha 2 \quad (6)$$

where x2, y2, and z2 are the position coordinates of the wrist relative to the elbow joint, r2 is the length of the lower arm, and α2 and β2 are elevation and azimuth angles of G2.

10. The system of claim 9, wherein:
the data logger receives the x1, y1 and z1 position coordinates from G1's RF transceiver and receives the x2, y2 and z2 position coordinates from G2's RF transceiver; and
the data logger's microcontroller calculates the wrist position relative to the shoulder joint using the following equations:

$$x = x1 + x2 \quad (7)$$

$$y = y1 + y2 \quad (8)$$

$$z = z1 + z2 \quad (9)$$

where x, y, and z are the position coordinates of the wrist relative to the shoulder joint.

11. The system of claim 4, including gyroscope torso angle measurement sensors, one mounted proximate to vertebra L1 and another mounted proximate to S1.

12. The system of claim 11, wherein:
each gyroscope torso angle measurement sensor includes a triaxial gyroscope (G3, G4) to measure the angular velocities, with G3 being mounted on vertebra L1 and G4 being mounted on vertebra S1; and
a microcontroller to calculate the angles of L1 and S1.

13. The system of claim 12, wherein each gyroscope torso angle measurement sensor further includes a radio frequency (RF) transceiver to transmit the L1 and S1 angle data to the data logger.

14. The system of claim 13, wherein:
the microcontroller associated with G3 calculates the pitch, yaw and roll angles of L1 by computing the integral of the pitch, yaw and roll angular velocities; and
the microcontroller associated with G4 calculates the pitch, yaw and roll angles of S1 by computing the integral of the pitch, yaw and roll angular velocities.

15. The system of claim 14, wherein:
the data logger receives the L1 and S1 pitch, yaw and roll angles from the L1 and S1 transceivers, and calculates the torso pitch, yaw and roll angles;
torso pitch angle is computed as the difference of the L1 and S1 pitch angles;
torso yaw angle is computed as the difference of the L1 and S1 yaw angles; and
torso roll angle is computed as the difference of the L1 and S1 roll angles.

16. The system of claim 1, including a wireless accelerometer sensor to measure torso acceleration.

17. The system of claim 1, including wireless foot force sensors to measure foot force distribution.

18. The system of claim 1, wherein the data logger performs an initial analysis of the sensor measurement data and wirelessly transfer the processed data to a smart phone.

19. The system of claim 18, wherein the data logger further transfers the processed data to a computer via a computer interface.

20. The system of claim 1, wherein the data logger is operative to wirelessly send commands via a Bluetooth module to a smart phone to dial an emergency number and send out a text message containing a prerecorded safety message, a summary of the data, corresponding GPS locations, and time stamps.

21. The system of claim 1, including a smart phone that can wirelessly receive and store the processed data from the data logger via its Bluetooth interface and transfer the saved data to a computer via a computer interface.

22. The system of claim 16, wherein:
the torso vibration sensor includes an accelerometer that measures the low-frequency acceleration of the lower back in real time;
a microcontroller that periodically calculates the root-mean-square (RMS) values of the acceleration; and
a transceiver that transmits the RMS acceleration data to the data logger at the end of each RMS period.

* * * * *